United States Patent [19]
Bass et al.

[11] Patent Number: 5,846,934
[45] Date of Patent: Dec. 8, 1998

[54] PURE SOMATOSTATIN ANTAGONIST AND METHODS OF USE THEREOF

[75] Inventors: Roy Tyson Bass, Somerset, N.J.; Brian Lee Buckwalter, Yardley, Pa.; John Richard Hadcock, Mt. Holly, N.J.; Bomi Pilloo Patel, Mumbai, India; John Francis Chiarello, Newtown, Pa.

[73] Assignee: American Cyanamid Company, Madison, N.J.

[21] Appl. No.: 801,374

[22] Filed: Feb. 19, 1997

Related U.S. Application Data

[60] Provisional application No. 60/011,978 Feb. 20, 1996.
[51] Int. Cl.[6] .......................... A61K 38/04; A61K 38/24; C07K 5/00; C07K 7/00
[52] U.S. Cl. .................................. 514/11; 514/16; 514/9; 530/313; 530/317; 530/328
[58] Field of Search ....................................... 530/313, 317, 530/328; 514/9, 16, 11

[56] References Cited

U.S. PATENT DOCUMENTS 4,508,711   4/1985   Coy et al. ................... 514/11

FOREIGN PATENT DOCUMENTS

WO 94/02163   2/1994   WIPO .

OTHER PUBLICATIONS

E. M. Ross, *The Pharmacological Basis of Therapeutics*, 8th Ed., Chapt. 2, Pergamon Press (1990).

Y. Cheng and W. H. Prusoff, Biochem. Pharmacol., 22, 3099–3108 (1973).

K. Yasuda, S. Rens–Damiano, C. D. Breder, S. F. Law, C. B. Saper, T. Reisine and G. I. Bell, J. Biol. Chem. 267, 20422–20428 (1992).

J. F. Bruno, Y. Xu, J. Song and M. Berelowitz, Proc. Nat'l. Aca. Sci. USA 89, 11151–11155 (1992).

A. M. O'Carrol, S. J. Lolait, M. König and L. Mahan, Mol. Pharmacol. 42, 939–946 (1992).

J. R. Hadcock, J. Strnad and C. M. Eppler, Mol. Pharmacol. 45, 410–416 (1994).

J. Strnad, C. M. Eppler, M. Corbett and J. R. Hadcock, Biochem. Biophys. Res. Commun. 191, 968–976 (1993).

B. L. Brown, J. D. M. Albano, R. P. Ekins and A. M. Sgherzi, Biochem. J. 121, 561–562 (1972).

*Primary Examiner*—Cecilia J. Tsang
*Assistant Examiner*—S. G. Marshall
*Attorney, Agent, or Firm*—Joseph M. Mazzarese

[57] ABSTRACT

A method for decreasing the effect of somatostatin. A peptide of formula I which is a pure somatostatin antagonist, methods for increasing the release of growth hormone, insulin and glucagon in mammals, and a method for the enhancement of growth in mammals are also described.

20 Claims, No Drawings

PURE SOMATOSTATIN ANTAGONIST AND METHODS OF USE THEREOF

This application claims priority from the co-pending provisional application Ser. No. 60/011,978 filed Feb. 20, 1996.

BACKGROUND OF THE INVENTION

Mammalian somatostatin, a tetradecapeptide, inhibits the release of growth hormone from the pituitary gland. It further inhibits the release of insulin and glucagon from the pancreatic islet cells. Most of the biological effects of somatostatin are mediated by five distinct somatostatin receptor (SSTR) subtypes. SSTR2 and SSTR5 are the predominant subtypes in peripheral tissues. Antagonists which are selective for individual somatostatin receptor subtypes may block only one or two subtypes, thereby decreasing the possibility of undesired side-effects.

Somatostatin agonists and antagonists are continually being sought to aid in the elucidation of the function of the hormone in controlling multiple physiological effects. In particular, a pure somatostatin antagonist, a compound which would successfully compete with the hormone at its receptor site, is of great interest. This compound could be used to block the inhibitory effects of somatostatin, which, in turn, would increase the release of growth hormone, insulin and glucagon. Although compounds have been discovered which demonstrate partial somatostatin antagonist activity, i.e., some agonist effect, some antagonist effect, no pure somatostatin antagonist has been described heretofore.

It is an object of this invention to provide a pure somatostatin antagonist.

It is another object of this invention to provide a method for decreasing the effect of somatostatin.

It is a further object of this invention to provide methods for increasing the release of growth hormone, insulin and glucagon in mammals and for enhancing growth in mammals.

It is another object of this invention to provide a pure somatostatin antagonist that is subtype selective.

Other objects and advantages of the present invention will be apparent to those skilled in the art from the description of the invention set forth below.

SUMMARY OF THE INVENTION

The present invention provides a method for decreasing the effect of somatostatin which comprises contacting the somatostatin receptor site with an effective amount of a peptide of formula I

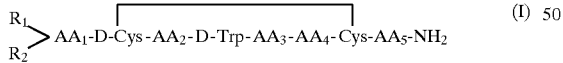

wherein $R_1$ and $R_2$ are each independently H, $C_1$–$C_8$alkyl, COR or COOR;

$AA_1$ is the D or L isomer of an aromatic α-amino acid optionally substituted with one to three $NO_2$, CN, Cl, Br, I, F, $COR_3$, $COOR_3$ or $OR_3$ groups;

$AA_2$ is the D or L isomer of an aromatic α-amino acid optionally substituted with one to three $NO_2$, CN, Cl, Br, I, F, $COR_4$, $COOR_4$ or $OR_4$ groups;

$AA_3$ is the D or L isomer of Arg, Lys, Orn or Cit;

$AA_4$ is Val, Leu, Ile, Abu, Nle, Thr, 3-$R_5$-Ser, Thr(Bzl) or Ser(Bzl), with the proviso that when $AA_4$ is Thr, then $AA_1$ must be the L isomer;

$AA_5$ is the D or L isomer of an aromatic α-amino acid optionally substituted with one to three $NO_2$, CN, Cl, Br, I, F, $COR_6$, $COOR_6$ or $OR_6$ groups, $N(CH_3)$Ala, $N(R_7)$-α-amino acid, Thr or Ser, with the proviso that the number of D-amino acid residues within the cyclic portion of the peptide is an even number;

R is $C_1$–$C_8$alkyl, phenyl, phenyl($C_1$–$C_4$)alkyl, naphthyl, or naphthyl ($C_1$–$C_4$) alkyl;

$R_2$, $R_3$, $R_4$, $R_6$ and $R_7$ are each independently H or $C_1$–$C_8$alkyl; and $R_5$ is H, $C_1$–$C_8$alkyl, or the D or L isomer of an aromatic α-amino acid optionally substituted with one to three $NO_2$, CN, Cl, Br, I, F, $COR_6$ or $OR_6$ groups; or the pharmaceutically acceptable salts thereof.

The present invention also provides peptides of formula (I) which demonstrate a pure somatostatin antagonistic effect, and methods for increasing the release of growth hormone, insulin and glucagon in mammals and for enhancing growth in mammals, which methods comprise administering an effective amount of a peptide of formula (I) to a mammal.

DETAILED DESCRIPTION OF THE INVENTION

One preferred embodiment of the present invention is a method for decreasing the effect of somatostatin comprising contacting the somatostatin receptor site with an effective amount of a peptide of formula I

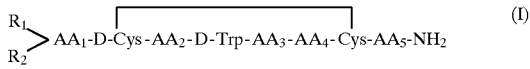

wherein $R_1$ and $R_2$ are each independently H, $C_1$–$C_8$alkyl, COR or COOR;

$AA_1$ is the D or L isomer of an aromatic α-amino acid optionally substituted with one to three $NO_2$, CN, Cl, Br, I, F, $COR_3$, $COOR_3$ or $OR_3$ groups;

$AA_2$ is the D or L isomer of an aromatic α-amino acid optionally substituted with one to three $NO_2$, CN, Cl, Br, I, F, $COR_4$, $COOR_4$ or $OR_4$ groups;

$AA_3$ is the D or L isomer of Arg, Lys, Orn or Cit;

$AA_4$ is Val, Leu, Ile, Abu, Nle, Thr, 3-$R_5$-Ser, Thr(Bzl) or Ser(Bzl), with the proviso that when $AA_4$ is Thr, then $AA_1$ must be the L isomer;

$AA_5$ is the D or L isomer of an aromatic α-amino acid optionally substituted with one to three $NO_2$, CN, Cl, Br, I, F, $COR_6$, $COOR_6$ or $OR_6$ groups, $N(CH_3)$Ala, $N(R_7)$-α-amino acid, Thr or Ser, with the proviso that the number of D-amino acid residues within the cyclic portion of the peptide is an even number;

R is $C_1$–$C_8$alkyl, phenyl, phenyl($C_1$–$C_4$)alkyl, naphthyl, or naphthyl ($C_1$–$C_4$) alkyl;

$R_2$, $R_3$, $R_4$, $R_6$ and $R_7$ are each independently H or $C_1$–$C_8$alkyl; and $R_5$ is H, $C_1$–$C_8$alkyl, or the D or L isomer of an aromatic α-amino acid optionally substituted with one to three $NO_2$, CN, Cl, Br, I, F, $COR_6$ or $OR_6$ groups; or the pharmaceutically acceptable salts thereof.

Advantageously, the peptides of formula I are selective for somatostatin subtypes SSTR2 and SSTR5. That is, they tend to bind more tightly to SSTR2 and SSTR5 and demonstrate weaker binding to SSTR1 and SSTR3. These unique binding properties allow the formula I peptides to act as pure somatostatin antagonists while decreasing the possiblity of undesirable side-effects.

The term "aromatic α-amino acid" designates an amino acid residue of formula II shown below

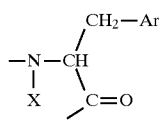

(II)

wherein X represents a bond in terminal amino acid $AA_1$ and H in non-terminal amino acids, $AA_{2-5}$ and Ar is a moiety containing an optionally substituted aromatic ring. Examples of Ar include, but are not limited to, the following structures wherein Yn represents n optional Y substituents and n is 0, 1, 2, or 3:

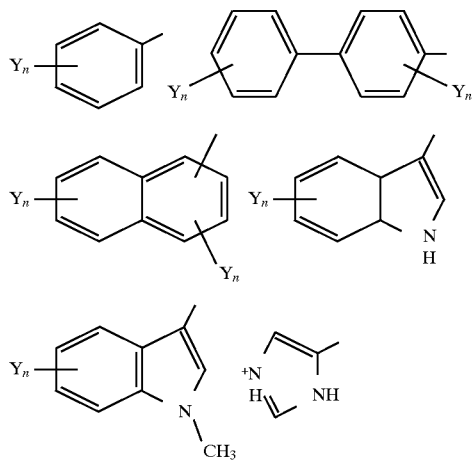

The term "pharmaceutically acceptable salts" designates non-toxic acid addition salts or metal complexes which are commonly used in the human and veterinary pharmaceutical industry. Illustrative examples of acid addition salts are those organic acids such as acetic, lactic, pamoic, maleic, citric, malic, ascorbic, succinic, benzoic, palmitic, suberic, salicylic, tartaric, methanesulfonic, toluenesulfonic acid or the like; those polymeric acids such as tannic acid, carboxymethyl cellulose or the like; and those inorganic acids such as hydrochloric acid, hydrobromic acid, sulfuric acid phosphoric acid or the like. Metal complexes include zinc, iron and the like.

The notations used for the peptide amino acid residues are those abbreviations commonly used in the art and include, but are not limited to, those listed on the table shown below.

| Abbreviation | Amino Acid |
|---|---|
| Ala | L-Alanine |
| Abu | L-2-Aminobutyric acid |
| Arg | L-Arginine |
| Cit | L-Citrulline |
| Cys | L-Cysteine |
| Ile | L-Isoleucine |
| Leu | L-Leucine |
| Lys | L-Lysine |
| Nal (1) | β-(1-Naphthyl) alanine |
| Nal (2) | β-(2-Naphthyl) alanine |
| Phe | L-Phenylalanine |
| Ser | L-Serine |
| Thr | L-Threonine |
| Trp | L-Tryptophan |
| Tyr | L-Tyrosine |
| Val | L-Valine |

Further, standard nomenclature and abbreviations used in the specification and claims include, but are not limited to, the following:

| Abbreviation | Structure |
|---|---|
| Ac | $CH_3C(O)-$ |
| Napc | (2-naphthoyl) |
| Nal (2) | (β-(2-naphthyl)alanyl) |
| N(CH$_3$)Ala | (N-methyl alanyl) |
| Cit | (citrullyl) |

Certain peptides of formula I have been described as neuromedin B receptor antagonists by D. H. Coy and J. E. Taylor in WO 94/02163. Methods to prepare said peptides are also described therein.

Surprisingly, the peptides having formula Ia and formula Ib, heretofore undisclosed, demonstrate pure somatostatin antagonist activity.

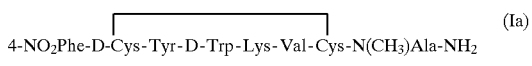

(Ia) 4-NO$_2$Phe-D-Cys-Tyr-D-Trp-Lys-Val-Cys-N(CH$_3$)Ala-NH$_2$

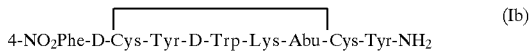

(Ib) 4-NO$_2$Phe-D-Cys-Tyr-D-Trp-Lys-Abu-Cys-Tyr-NH$_2$

Advantageously the formula Ia and Ib peptides may be used to decrease the effects of mammalian somatostatin, thereby increasing the production of growth hormone, insulin and glucagon in mammals. Further, the formula Ia and Ib peptides of the invention are SSTR2 and SSTR5 selective. Subtype selective somatostatin antagonists such as the formula Ia and Ib peptides may selectively increase the production of growth hormone, insulin or glucagon and thereby decrease the possibility of undesirable side-effects.

Conveniently, the formula Ia and Ib peptides of the invention may be prepared according to standard peptide synthesis methods known in the art such as those described in U.S. Pat. No. 4,508,711 or WO 94/02163.

In actual practice, the peptides of formula I, including Ia and Ib, may be used to block somatostatin inhibition of growth hormone release, thereby effectively facilitating growth in target species. For example, an increase in the levels of growth hormone, insulin, and glucagon in a mammalian host may be obtained when the formula I peptide is administered thereto at dosages of about $2 \times 10^{-6}$ mg/kg to 10.0 mg/kg of mammalian body weight per day. Said peptide may be administered orally in the form of a feed additive or as a bolus, implant, pill, tablet, oral gel, or the like. Also contemplated is administration by parenteral intramuscular, subcutaneous, intraperitoneal or intravenous injection, or as a transdermal application or nasal spray.

In order to present a more clear understanding of the invention, the following specific examples are set forth below. These examples are merely illustrative and are not to be understood as limiting the scope and underlying principles of the invention in any way. Indeed, various modifications of the invention in addition to those illustrated and described herein will become apparent to persons skilled in the art from the following examples and the foregoing description. Such modifications are also intended to fall within the scope of the appended claims.

The term, HPLC, designates high performance liquid chromatography.

EXAMPLE 1

Preparation of

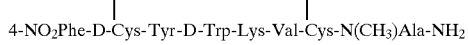
4-NO$_2$Phe-D-Cys-Tyr-D-Trp-Lys-Val-Cys-N(CH$_3$)Ala-NH$_2$

Step 1: Preparation of H-p-NO$_2$Phe-S-trityl-D-Cys-O-t-butyl-Tyr-O-Trp-Nε-t-butyloxycarbonyl-Lys-Val-S-trityl-Cys-N(CH$_3$)Ala-PAL resin Fmoc-PAL-PEG-resin (Millipore) (1.8 g, 0.32 mmole) is placed in the reaction vessel of a Millipore 9050 peptide synthesizer programmed to perform the following continuous flow reaction cycle: (a) Dimethylformamide (DMF) wash; (b) 20% piperidine in DMF wash (2 times for 3 minutes and 5 minutes each); (c) DMF wash.

The Fmoc deblocked resin is exposed to a continuous-flow solution of 9-fluorenylmethoxycarbonyl-N(CH$_3$) Ala (Fmoc-N-Me-Ala-OH) (Advanced Chemtech) benzotriazol-1-yloxy-tris(dimethylamino)-phosphonium hexafluorophosphate (BOP)(Richelieu Biotechnologies, Inc.), 1-hydroxybenzotriazole (HOBT), and diisopropyl-ethylamine in DMF for 30 minutes and the resulting amino acid resin is then cycled through steps (a) through (c) in the above wash program. The following amino acids (1.3 mmol) are coupled successively by the same procedure: Fmoc-S-trityl-Cys-OH, Fmoc-Val-OH, Fmoc-Nε-t-butyloxycarbonyl-Lys-OH, Fmoc-D-Trp-OH, Fmoc-o-t-butyl-Tyr-OH, Fmoc-S-trityl-D-Cys-OH, Fmoc-p-NO$_2$Phe-OH. The resin is washed with Methylene chloride and dried to give a dry weight of 2 g.

Step 2: Preparation of H-p-No$_2$Phe-D-Cys-Tyr-D-Trp-Lys-Val-Cys-N(CH$_3$) Ala-NH$_2$ The peptide resin obtained in Step 1 (2g, 0.3 mmole) is mixed with ethanodithiol and trifluoroacetic acid at 25° C., stirred for 3 hours, and filtered. The filtrate containing the peptide is evaporated and the peptide is precipitated with ether. The crude peptide is then dissolved in 50 mL dimethyl sulfoxide with 200 mL water and stirred at 25° C. for 3 days. This solution is concentrated and applied to a Rainin 21.4× 250 mm, octadecylsilane silica (12 μm) preparative high performance liquid chromatography column followed by elution with a linear gradient of acetonitrile in 0.1% aqueous trifluoroacetic acid solution. The fraction containing the desired peptide is evaporated and the peptide is precipitated with ether to give 31 mg of the title product as an amorphous off-white solid, homogeneous by analytical HPLC. The peptide is identified by electrospray mass spectrometry analysis.

EXAMPLE 2

Preparation of

4-NO$_2$Phe-D-Cys-Tyr-D-Trp-Lys-Abu-Cys-Tyr-NH$_2$

Using essentially the same procedure described in Example 1 and substituting Fmoc-Tyr-OH and Fmoc-Abu-OH in place of Fmoc-N(CH$_3$)Ala-OH and Fmoc-Val-OH, respectively, the title product is obtained as a white amorphous solid, 36 mg, homogeneous by analytical HPLC. The peptide is identified by electrospray mass spectrometry analysis.

EXAMPLE 3

Evaluation of Somatostatin Agonist and Somatostatin Antagonist Activity of Test Compounds Using Modified Yeast Cells In this evaluation, yeast cells which have been specifically modified to functionally express rat somatostatin receptor subtype 2 (SSTR2) on their cell surfaces are used. S. Cerevisiae LY364 cells are plated in a standard synthetic agar medium which lacks histidine. In the absence of a somatostatin receptor agonist, the auxotrophic (his3) cells are unable to grow. In the presence of somatostatin, or a somatostatin agonist, the expression of an enzyme (His3p: imidazole-glycerol phosphate dehydratase) which is essential for histidine biosynthesis is induced. The cells become competent to produce histidine, resulting in a zone of growing cells around the applied test compound. The zone is measured and the test compound is given an agonist rating on a scale of 1–5 wherein 1 is minimum agonist activity and 5 is maximum agonist activity.

To evaluate the somatostatin antagonist activity of a test compound, the above procedure is followed except on day 3, 5 μL of 1 mg/mL of somatostatin, S-14, is added to each plate, before applying the test compound. If the test compound is an antagonist of somatostatin, then a zone of no growth will appear within the cell growth zone. This zone of no growth is measured and the test compound is given an antagonist rating on a scale of 1–5 wherein 1 is minimum antagonist activity and 5 is maximum antagonist activity.

The results are shown in Table I. When no activity is observed, the result is indicated by a dash.

Materials and Methods

SCD-ura-trp:
1) To 500 mL water add:
   1. 7 g YNB without amino acids and (NH$_4$)$_2$SO$_4$
   5.0 g (NH$_4$)$_2$SO$_4$
   0.7 g CSM-ura-trp
2) To additional 500 mL water add:
   20 g Dextrose
3) Autoclave separately. Mix.

SCL-ura-trp:
1) To 500 mL water add:
   1.7 g YNB without amino acids and (NH$_4$)$_2$S$_4$
   5.0 g (NH$_4$)$_2$SO$_4$
   0.7 g CSM-ura-trp
2) To additional 500 mL water add:
   30 mL Lactic Acid
3) Autoclave separately. Mix.

SCG-ura-trp:
1) To 500 mL water add:
   1.7 g YNB without amino acids and (NH$_4$)$_2$SO$_4$
   5.0 g (NH$_4$)$_2$SO$_4$
   0.7 g CSM-ura-trp
2) To additional 500 mL water add:
   30 g D-Galactose
3) Autoclave separately. Mix.

SCG-ura-trp-his agar medium, pH 6.8:
1) To 500 mL water add:
   1.7 g YNB without amino acids and (NH$_4$)$_2$SO$_4$
   5.0 g (NH$_4$)$_2$SO$_4$
   0.7 g CSM-ura-trp-his Stirring Bar 2) Adjust pH to 6.8–6.9 by dropwise addition of conc. NH$_4$OH 3) To additional 500 mL water add:
   30 g D-Galactose, 20 g Agar 4) Autoclave separately.

5) Stir to mix thoroughly.

6) Equilibrate temperature to 55° C.

YNB without amino acids and (NH$_4$)$_2$SO$_4$, CSM-ura-trp, and CSM-ura-trp-his are manufactured by Bio101. Ammonium sulfate ((NH$_4$)$_2$SO$_4$), Dextrose (D-glucose), D-Galactose, and Lactic Acid are manufactured by Sigma.

Protocol:

Day 1.

1) Inoculate 2 mL SCD-ura-trp liquid medium in Falcon 2051 tube with a single colony taken from a plate containing LY364 (MATa ura3-52 leu2 his3 trp1 lys2 ade2 far1:: LYS2 fus1:: FUS1-HIS3 gpa1::hisG sst2::.ADE2 bearing the SSTR2 expression plasmid, pJH2, and the G protein expression plasmid, pLP82) cells.

2) Incubate overnight in a roller drum at 30° C.

Day 2.

1) Harvest the cells by centrifugation (3 krpm, 5 min, room temp).

2) Re-suspend with 5 mL of sterile water.

3) Harvest again by centrifugation.

4) Re-suspend in 5 mL SCL-ura-trp liquid medium.

5) Incubate for 6 hours in a roller drum at 30° C.

6) Harvest the cells again by centrifugation.

7) Re-suspend in 5 mL SCG-ura-trp liquid medium.

8) Incubate overnight in a roller drum at 30° C.

Day 3.

1) Autoclave SCG-ura-trp-his pH 6.8 agar medium.

2) Cool to 55° C. in water bath.

3) Add 1 mL of LY364 culture to 1 liter of agar medium.

4) Stir vigorously for 1 min.

5) Pour 150 mL each into five 500 cm$^2$ plates.

6) Allow to cool on level surface.

7) Apply test compound. [Somatostatin-14 (10 μL of a 1 mg/mL solution of S-14 in sterile water) applied to the surface of the plate will give rise to a zone of growth 2.5–3 cm in diameter.]

8) Incubate plates at 30° C.

Antagonist Assay

On day 3, add 5 μL 1 mg/mL S-14 to each plate.

Day 5. Begin checking plates for growth around applied compounds.

Day 7. Growth in response to somatostatin should be readily observable. Rate extent of growth or inhibition of growth according to rating scale described hereinabove.

TABLE I

AA$_1$—D—Cys—AA$_2$—D—Trp—AA$_3$—AA$_4$—Cys—AA$_5$—NH$_2$

| Test Compound | | | | | Yeast Assay | |
|---|---|---|---|---|---|---|
| AA$_1$ | AA$_2$ | AA$_3$ | AA$_4$ | AA$_5$ | Agonist | Antagonist |
| 4-NO$_2$Phe | Tyr | Lys | Val | N(CH$_3$)Ala | — | 3 |
| 4-NO$_2$Phe | Tyr | Lys | Val | Tyr | — | 5 |
| 4-NO$_2$-D—Phe | Tyr | Lys | Val | Tyr | — | 2 |
| D-Nal(2) | Tyr | Lys | Val | Tyr | — | 2 |
| L-Nal(2) | Tyr | Lys | Val | Tyr | — | 3 |
| 4-NO$_2$Phe | Tyr | Lys | Thr | Tyr | — | 5 |
| 4-NO$_2$Phe | Tyr | Lys | Val | Nal(2) | — | 2 |
| 4-NO$_2$Phe | Tyr | Lys | Ser | Nal(2) | — | 3 |
| 4-NO$_2$Phe | Tyr | Orn | Val | Tyr | — | 1 |
| NMe-4-NO$_2$Phe | Tyr | Lys | Val | Tyr | — | 5 |
| 4-NO$_2$Phe | Tyr | Lys | Abu | Tyr | — | 3 |
| 4-NO$_2$Phe | Tyr | Lys | Thr | D-Tyr | — | 4 |
| L-Nal(2) | Tyr | Lys | Thr | Tyr | — | 1 |
| 4-NO$_2$Phe | Tyr | Arg | Thr | Tyr | — | 2 |
| Ac-4-NO$_2$Phe | Tyr | Lys | Thr(Bzl) | D-Tyr | — | 3 |
| Ac-4-NO$_2$Phe | Tyr | Lys | Tyr | D-Thr | — | 1 |
| Ac-4-IPhe | Tyr | Lys | Thr | Tyr | — | 1 |
| Ac-4-NO$_2$Phe | Tyr | Lys | Thr | D-Tyr | — | 4 |
| Ac-Nal(2) | Tyr | Lys | Thr | Tyr | — | 1 |
| Ac-4-NO$_2$Phe | Tyr | Arg | Thr | Tyr | — | 1 |
| Ac-4-NO$_2$Phe | Tyr | Lys | Thr | Tyr | — | 2 |
| 4-IPhe | Tyr | Lys | Thr | Tyr | — | 5 |
| Napc-4-NO$_2$Phe | Tyr | Lys | Thr | Tyr | — | 1 |
| Ac-Nal(2) | Tyr | Lys | Thr | D-Tyr | — | 3 |
| Nal(2) | Tyr | Lys | Thr | D-Tyr | — | 3 |
| Ac-Nal(1) | Tyr | Lys | Thr | Tyr | — | 2 |
| Nal(1) | Tyr | Lys | Thr | Tyr | — | 4 |
| Napc-4-IPhe | Tyr | Lys | Thr | D-Tyr | — | 2 |
| Ac-4-IPhe | Tyr | Lys | Thr | D-Tyr | — | 4 |
| 4-NO$_2$Phe | Tyr | Lys | Tyr | D-Tyr | — | 3 |
| 4-NO$_2$Phe | Tyr | Lys | Thr(Bzl) | D-Tyr | — | 4 |
| Ac-4NO$_2$Phe | Tyr | Lys | Tyr | D-Tyr | — | 3 |

EXAMPLE 4

Evaluation Of Competitive Binding Activity Of Test Compounds

In this evaluation the concentration of test compound required to displace 50% of somatostatin, SRIF, from the SRIF receptor subtypes expressed in mammalian cells is measured, i.e., the concentration required to inhibit 50% of [$^{125}$I] Tyr$^{11}$ S-14 (Amersham) (IC$_{50}$) from binding to the SRIF receptor subtypes.

Radiolabeled SRIF is mixed with pituitary cells, the test compound is added, the mixture is incubated and the radioactivity is measured as compared to control. Reduced radioactivity indicates successful competitive binding of the test compound to the pituitary cell receptor. The concentration of the test compound in nanomolar units required to displace 50% of SRIF from the pituitary cell receptor is calculated and reported in Table II as the IC$_{50}$ value. Also calculated is the inhibitory constant, K$_i$. The more potent antagonistic activity demonstrated, the lower the IC$_{50}$ and K$_i$ value.

Protocol:

All radioligand binding assays are performed in 96-well microtiter plates using a binding buffer (50 mM HEPES, pH 7.4, 5 mM MgCl$_2$, 0.25% BSA) containing protease inhibitors (5 µg/mL leupeptin, 5 µg/mL aprotinin, 100 µg/mL bacitracin, and 100 µg/mL benzamidine. In this evaluation, [$^{125}$I] Tyr$^{11}$S-14 (Amersham) is used because [$^{125}$I]S-28 displays very high non-specific binding in filtration assays (>75%). All components are diluted in a binding buffer containing protease inhibitors and added to the microtiter plate wells in the following order: 20 µL binding buffer (for no competitor well) or 20 µL non-radiolabeled S-14 or competitor(1×10$^{-12}$M to 1×10$^{-5}$M final concentration), then 10 µL [$^{125}$I] Tyr$^{11}$S-14 (150,000 cpm at 2000 Ci/mmole, 250 pM final concentration). The binding reaction is initiated by adding 2–60 µg of membrane protein in a 170 µL volume. Final reaction volume is 200 µl/well. All incubations are carried out at room temperature for 2 hours. Free radioligand is separated from bound ligand by rapid filtration through a glass fiber filter (IH-201-HA) using an Inotech cell harvester. The filter is then washed several times with cold (4° C.) binding buffer lacking BSA and protease inhibitors prior to counting in an LKB gamma master counter (78% efficiency). Whatman GFC filters presoaked in 0.3% polyethylenimine (to decrease background) are used.

The IC$_{50}$ values and K$_i$ values are calculated using the well-known methods described by Y. Cheng and W. H. Prusoff, Biochem. Pharmacol. 22, 3099–3108 (1973), incorporated herein by reference thereto.

TABLE II

AA$_1$—D—Cys—AA$_2$—D—Trp—AA$_3$—AA$_4$—Cys—AA$_5$—NH$_2$

| Test Compound | | | | | | SSTR2 Binding Affinity |
|---|---|---|---|---|---|---|
| AA$_1$ | AA$_2$ | AA$_3$ | AA$_4$ | AA$_5$ | IC$_{50}$ | K$_i$ nanomolar |
| 4-NO$_2$Phe | Tyr | Lys | Val | N(CH$_3$)Ala | 55 | 24.44 |
| 4-NO$_2$Phe | Tyr | Lys | Val | Tyr | 29 | 12.89 |
| 4-NO$_2$-D—Phe | Tyr | Lys | Val | Tyr | 39 | 17.33 |
| D-Nal(2) | Tyr | Lys | Val | Tyr | 2 | 0.89 |
| L-Nal(2) | Tyr | Lys | Val | Tyr | 5 | 2.22 |
| 4-NO$_2$Phe | Tyr | Lys | Thr | Tyr | 3 | 1.33 |
| 4-NO$_2$Phe | Tyr | Lys | Ser | Nal(2) | 10 | 4.44 |
| 4-NO$_2$Phe | Tyr | Orn | Val | Tyr | 113 | 50.22 |
| NMe-4-NO$_2$Phe | Tyr | Lys | Val | Tyr | 6 | 2.67 |

TABLE II-continued

AA$_1$—D—Cys—AA$_2$—D—Trp—AA$_3$—AA$_4$—Cys—AA$_5$—NH$_2$

| Test Compound | | | | | | SSTR2 Binding Affinity |
|---|---|---|---|---|---|---|
| AA$_1$ | AA$_2$ | AA$_3$ | AA$_4$ | AA$_5$ | IC$_{50}$ | K$_i$ nanomolar |
| 4-NO$_2$Phe | Tyr | Lys | Abu | Tyr | 4 | 1.78 |
| 4-IPhe | Tyr | Lys | Thr | Tyr | 0.6 | 0.26 |
| Ac4-IPhe | Tyr | Lys | Thr | D-Tyr | 6 | 2.80 |
| 4-NO$_2$Phe | Tyr | Lys | Val | Nal(2) | 7 | 3.10 |
| 4-NO$_2$Phe | Tyr | Lys | Thr | D-Tyr | 3 | 1.50 |
| L-Nal(2) | Tyr | Lys | Thr | Tyr | 0.9 | 0.40 |
| Ac-4-NO$_2$Phe | Tyr | Lys | Thr | D-Tyr | 0.7 | 0.30 |
| Ac-Nal(2) | Tyr | Lys | Thr | Tyr | 1 | 0.48 |
| 4-NO$_2$Phe | Tyr | Arg | Thr | Tyr | 57 | 25.00 |

EXAMPLE 5

Evaluation Of The Effect Of Test Compounds On Cyclic AMP Accumulation

Cyclic AMP accumulation assays are used to determine the functional coupling of somatostatin receptors to effectors. All five cloned somatostatin receptors inhibit cyclic AMP accumulation and adenylyl cyclone activity.[1,2,3,4,5] This evaluation measures cyclic AMP accumulation from intact cells using the adrenal binding protein method. Signal transduction by somatostatin is mediated by lowering intracellular c-AMP levels. This functional assay measures the ability of the test compound to inhibit the effect of somatostatin on forskalin stimulated c-AMP levels.

Preparation of Adrenal Binding Protein

Bovine adrenal gland extracts are prepared according to the method of Brown et al[6] with minor modifications. Hence, bovine adrenal glands are purchased from Pel Freez and shipped on dry ice. Two-four adrenals are thawed and the cortices are separated on ice: chopped into small pieces; resuspended in 1.5 volumes of buffer containing 0.25M sucrose, 50 mM Tris-HCl pH 7.4, 25 mM KCl, 5 mM MgCl$_2$ and protease inhibitors (5 µg/ml leupeptin, 5 µg/ml aprotinin, 100 µg/ml bacitracin, and 100 µg/ml benzamidine; homogenized with a Polytron and centrifuged for 5 minutes. The resultant supernatant is saved and centrifuged for 15 minutes. This resultant supernatant is saved and stored as 1 mL aliquots at −80° C. Four adrenals glands are usually sufficient to prepare 30–50 one mL aliquots. Each preparation is tested with standards at different dilutions before use in the following experiment.

Preparation Of Cells For Cyclic AMP Accumulations

Somatostatin-mediated inhibition of cyclic AMP accumulation is measured in intact cells co-incubated with the diterpene forskalin (5 µM) which activates adenylyl cyclase directly and stimulates cyclic AMP accumulation in cells. The medium is aspirated from two 100 mm plates of cells, a 5 mL portion of phosphate-buffered saline containing 2 mM EDTA is added to each plate. The cells are washed off the plate, without scraping. The cells are then pelleted and resuspended in Kreb's Ringers Phosphate (KRP) containing 2 mM CaCl$_2$ (added fresh), washed once and resuspended in 2 ml of KRP with a CaCl$_2$ containing 100 µM IBMX. The cells are counted and the concentration of cells is adjusted to 50,000/70 µl and incubated 15 minutes at room temperature before starting the assay.

Generation Of Cyclic AMP

Polypropylene tubes (12×75) are labelled (test samples are done in triplicate including controls). Test samples are prepared containing the following: no added peptide sample (basal), forskalin alone (10 μM final), and forskalin plus various amounts of S-14 (1×10$^{-10}$M to 1×10$^{-6}$μM, final). The first two steps are done on the bench top. Volumes are adjusted with KRP and 10 μl 1 mM IBMX is added to each tube. The tubes are placed in a shaking 37° C. water bath and 70 μl cells is added at 15 second intervals until final volume/tube is 100 μL (concentration of cells is 25–100,000/tube). The tubes are incubated for 15 minutes at 37° C., treated with 10 μl of 1.0N HCl at 10 second intervals and transfered to an ice bath for 3 minutes (tubes may be stored overnight). The samples are neutralized with 10 μl 1.0N NaOH containing 250 mM Tris, pH 7.4.

Cyclic AMP Assay

The test tube racks are placed half way down in a large chest of ice. A 50 μl portion of cyclic AMP standard (Sigma) is aliquoted to each tube in triplicate (e.g. 0, 0.5, 1.0, 2.0, 4.0, 8.0, 16.0 pmoles/tube), then 70 μl KRP is added to each tube of standard. One set of tubes containing 220 μl KRP is set up for the background. A 50 μl portion of 10 nM [$^3$H]cyclic AMP (Amersham) is added to all tubes (standards and test samples). Adrenal Binding Protein (diluted 1:15 with ice cold 20 mM KH$_2$PO$_4$ pH 6.0 (100 μl) is added to all tubes except the background tubes Each tube is-incubated for 120 minutes on ice, treated with 100 μl charcoal/BSA solution (90 mg BSA, 180 mg Norit A, 30 ml 20 mM KH$_2$PO$_4$ pH 6.0), and vortexed for 10 seconds (spun for 3 minutes at 2000 X g in a refrigerated centrifuge at 4° C.). The supernatant is decanted into scintillation vials containing 5 ml of Ecoscint and quantified by liquid scintillation spectrometry. A standard curve is generated by plotting the concentration of the c-AMP standard along the x axis and the log cpm generated by each concentration along the y axis. Individual test sample results are calculated from the standard curve generated during each experiment. The data is expressed in values of pmoles/10$^6$ cells.

Using this data, the % intrinsic activity (%IA) for each test sample is calculated[7] and reported in Table III. An asterisk, *, indicates the test was not run.

The below-listed references are incorporated herein by reference thereto.

[1] K. Yasuda, S. Rens-Damiano, C. D. Breder, S. F. Law, C. B. Saper, T. Reisine and G. I. Bell, J. Biol. Chem. 267, 20422–20428 (1992).

[2] J. F. Bruno, Y. Xu, J. Song and M. Berelowitz, Proc. Natl. Acad. Sci. USA 89, 11151–11155 (1992).

[3] A. M. O'Carrol, S. J. Lolait, M. König and L. Mahan, Mol. Pharmacol. 42, 939–946 (1992).

[4] J. R. Hadcock, J. Strnad and C. M. Eppler, Mol. Pharmacol. 45, 410–416 (1994).

[5] J. Strnad, C. M. Eppler, M. Corbett and J. R. Hadcock, Biochem. Biophys. Res. Commun.191, 968–976 (1993).

[6] B. L. Brown, J. D. M. Albano, R. P. Ekins and A. M. Sgherzi, Biochem. J. 121, 561–562 (1971).

[7] E. M. Ross, The Pharmacological Basis of Therapeutics, [8]th Ed., Chapt. 2, Pergamon Press (1990).

TABLE III

| AA$_1$—D—Cys—AA$_2$—D—Trp—AA$_3$—AA$_4$—Cys—AA$_5$—NH$_2$ | | | | | |
|---|---|---|---|---|---|
| Test Compound | | | | | SSTR$^2$ |
| AA$_1$ | AA$_2$ | AA$_3$ | AA$_4$ | AA$_5$ | % IA |
| 4-NO$_2$Phe | Tyr | Lys | Val | N(CH$_3$)Ala | 29 |
| 4-NO$_2$Phe | Tyr | Lys | Val | Tyr | 11 |

TABLE III-continued

| AA$_1$—D—Cys—AA$_2$—D—Trp—AA$_3$—AA$_4$—Cys—AA$_5$—NH$_2$ | | | | | |
|---|---|---|---|---|---|
| Test Compound | | | | | SSTR$^2$ |
| AA$_1$ | AA$_2$ | AA$_3$ | AA$_4$ | AA$_5$ | % IA |
| 4-NO$_2$-D—Phe | Tyr | Lys | Val | Tyr | 42 |
| D-Nal(2) | Tyr | Lys | Val | Tyr | 8 |
| L-Nal(2) | Tyr | Lys | Val | Tyr | 13 |
| 4-NO$_2$Phe | Tyr | Lys | Thr | Tyr | 5 |
| 4-NO$_2$Phe | Tyr | Lys | Ser | Nal(2) | 7 |
| 4-NO$_2$Phe | Tyr | Orn | Val | Tyr | * |
| NMe-4-NO$_2$Phe | Tyr | Lys | Val | Tyr | 9 |
| 4-NO$_2$Phe | Tyr | Lys | Abu | Tyr | 21 |
| 4-IPhe | Tyr | Lys | Thr | Tyr | -12 |
| Ac4-IPhe | Tyr | Lys | Thr | D-Tyr | * |
| 4-NO$_2$Phe | Tyr | Lys | Val | Nal(2) | 8 |
| 4-NO$_2$Phe | Tyr | Lys | Thr | D-Tyr | 12 |
| L-Nal(2) | Tyr | Lys | Thr | Tyr | * |
| Ac-4-NO$_2$Phe | Tyr | Lys | Thr | D-Tyr | -3 |
| Ac-Nal(2) | Tyr | Lys | Thr | Tyr | -26 |
| 4-NO$_2$Phe | Tyr | Arg | Thr | Tyr | * |

What is claimed is:

1. A method for decreasing the effect of somatostatin which comprises contacting the somatostatin receptor site with an effective amount of a peptide of formula I

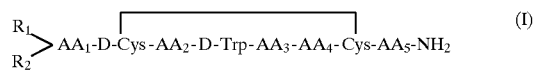

wherein

R$_1$ and R$_2$ are each independently H, C$_1$–C$_8$alkyl, COR or COOR;

AA$_1$ is the D or L isomer of an aromatic α-amino acid of formula II $$\begin{array}{c} \phantom{-N-}CH_2-Ar \\ \phantom{-N-}/ \\ -N-CH \\ | \phantom{-CH}\backslash \\ \phantom{-N-CH}C=O \end{array} \quad (II)$$

wherein Ar represents a moiety selected from the group consisting of

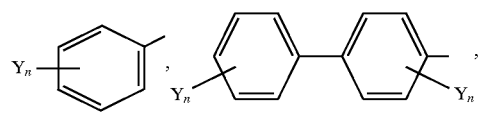

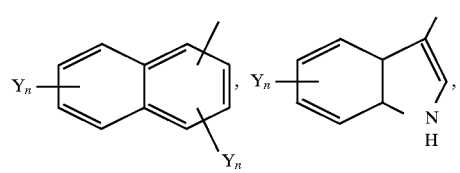

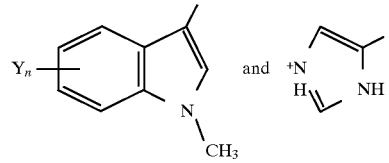

wherein n is 0, 1, 2, or 3 and each substituent Y independently represents NO$_2$, CN, Cl, Br, I, F, COR$_3$, COOR$_3$ or OR$_3$ groups;

AA₂ is the D or L isomer of an aromatic α-amino acid of formula IIa

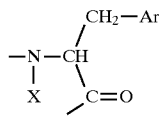  (IIa)

wherein X is H, Ar and n are as defined above, and each substituent Y independently represents NO₂, CN, Cl, Br, I, F, COR₄, COOR, or OR4 groups;

AA₃ is the D or L isomer of Arg, Lys, Orn or Cit;

AA₄ is Val, Leu, Ile, Abu, Nle, Thr, 3-R5-Ser, Thr(Bzl) or Ser(Bzl), with the proviso that when AA₄ is Thr, then AA₁ must be the L isomer;

AA₅ is the, D or L isomer of an aromatic α-amino acid of formula Ia wherein X is H, Ar and n are as defined above, and each substituent Y independently represents NO₂, CN, Cl, Br, I, F, COR₆, COOR₆ or OR₆ groups, N(CH₃)Ala, N(R₇)-α-amino acid, Thr or Ser, with the proviso that the number of D-amino acid residues within the cyclic portion of the peptide is an even number;

R is C₁C₈alkyl, phenyl, phenyl(C₁–C₄)alkyl; naphthyl, or naphthyl(C₁–C₄)alkyl;

R₂, R₃, R₄, R₆ and R₇ are each independently H or C₁–C₈alkyl; and

R₅ is H, C₁–C₈alkyl, or the D or L isomer of an aromatic α-amino acid of formula IIa wherein X is H, Ar and n are as defined above, and each substituent Y independently represents NO₂, CN, Cl, Br, I, F, COR₆ or OR₆ groups; or the pharmaceutically acceptable salts thereof.

2. The method according to claim 1 wherein AA₁ is 4-NO₂Phe.

3. The method according to claim 1 wherein AA₅ is Tyr or N(CH₃)Ala.

4. The method according to claim 1 wherein AA₄ is Val or Abu.

5. The method according to claim 1 wherein AA₂ is Tyr and AA3 is Lys.

6. The method according to claim 1 wherein said peptide is

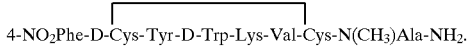

7. The method according to claim 1 wherein said peptide is

8. A peptide of formula Ia

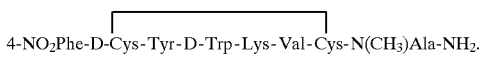  (Ia)

9. A peptide of formula Ib

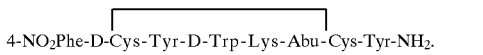  (Ib)

10. A method for increasing the release of growth hormone in mammals which comprises administering thereto an effective amount of a peptide of formula I as defined in claim 1.

11. The method according to claim 10 wherein said peptide is

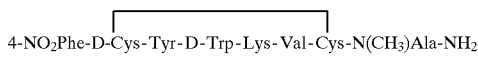

or

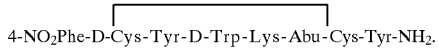

12. The method according to claim 10 wherein said effective amount is about 2×10⁻⁶ mg/kg to 10.0 mg/kg.

13. A method for increasing the release of insulin in mammals which comprises administering thereto an effective amount of a peptide of formula I as defined in claim 1.

14. The method according to claim 13 wherein said peptide is

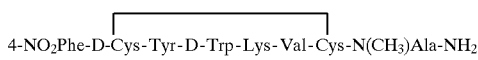

or

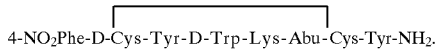

15. The method according to claim 13 wherein said effective amount is about 2×10⁻⁶ mg/kg to 10.0 mg/kg.

16. A method for increasing the release of glucagon in mammals which comprises administering thereto an effective amount of a peptide of formula I as defined in claim 1.

17. The method according to claim 16 wherein the peptide is

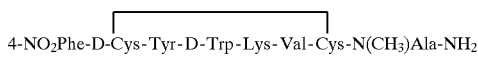

or

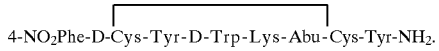

18. The method according to claim 16 wherein said effective amount is about 2×10⁻⁶ mg/kg to 10.0 mg/kg.

19. A method for enhancing the growth of mammals which comprises administering thereto an effective amount of a peptide of formula I as defined in claim 1.

20. The method according to claim 19 wherein said peptide is

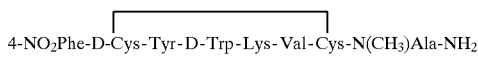

or

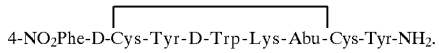

* * * * *